United States Patent
Croizat et al.

(10) Patent No.: US 8,845,604 B2
(45) Date of Patent: Sep. 30, 2014

(54) DEVICE FOR PROVIDING A VACUUM FOR VACUUM WOUND TREATMENT COMPRISING A HOLDING OR CARRYING DEVICE

(75) Inventors: Pierre Croizat, Herbrechtingen (DE); Axel Eckstein, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 13/484,293

(22) Filed: May 31, 2012

(65) Prior Publication Data

US 2012/0310188 A1    Dec. 6, 2012

Related U.S. Application Data

(60) Provisional application No. 61/457,846, filed on Jun. 17, 2011.

(30) Foreign Application Priority Data

Jun. 1, 2011 (DE) .......................... 10 2011 076 868

(51) Int. Cl.
*A45C 13/26* (2006.01)
*A61B 17/06* (2006.01)
*A61M 1/00* (2006.01)

(52) U.S. Cl.
CPC ....... *A61M 1/0088* (2013.01); *A61M 2209/088* (2013.01)
USPC .......................................... 604/319; 604/174

(58) Field of Classification Search
CPC ............. A45F 3/02; A45F 3/04; A45F 3/047; A45F 3/06; A45F 3/14; A45F 5/00; A45C 13/26; A61B 17/06

USPC ................................................... 604/319, 174
See application file for complete search history.

(56) References Cited

U.S. PATENT DOCUMENTS

| | | | |
|---|---|---|---|
| 6,038,745 A | 3/2000 | Rapp | |
| 2002/0008125 A1 | 1/2002 | Caputi | |
| 2010/0187065 A1* | 7/2010 | Pidgeon et al. | 190/115 |
| 2012/0209228 A1* | 8/2012 | Croizat et al. | 604/319 |

FOREIGN PATENT DOCUMENTS

| | | |
|---|---|---|
| DE | 73 35 721 | 3/1974 |
| DE | 37 18 477 | 6/1988 |
| DE | 43 14 014 | 8/1994 |
| DE | 296 18 961 | 2/1997 |
| DE | 10 2005 031 644 | 1/2007 |
| DE | 20 2006 015 816 | 1/2007 |
| DE | 10 2007 009 984 | 10/2007 |
| DE | 20 2010 002 855 | 6/2010 |
| WO | WO 2007/030599 | 3/2007 |

* cited by examiner

*Primary Examiner* — Leslie Deak
*Assistant Examiner* — Sara Sass
(74) *Attorney, Agent, or Firm* — Paul Vincent

(57) ABSTRACT

A portable device (2) for providing a vacuum for medical vacuum treatment of wounds on the body of a person or of an animal has a holding or carrying device (10) with two connecting sections (12, 14) on the housing, which are disposed on the housing part (4) for connection to two connecting sections of a holding or carrying strap on the strap, wherein the holding or carrying strap comprises a third strap-side connecting section, which is spaced apart from the opposing ends of the holding or carrying strap and from the first and second strap-side connecting sections disposed there, and arranged between these ends, for connection to one of the connecting sections on the housing and/or to a strap-side connecting section disposed at the end.

11 Claims, 4 Drawing Sheets

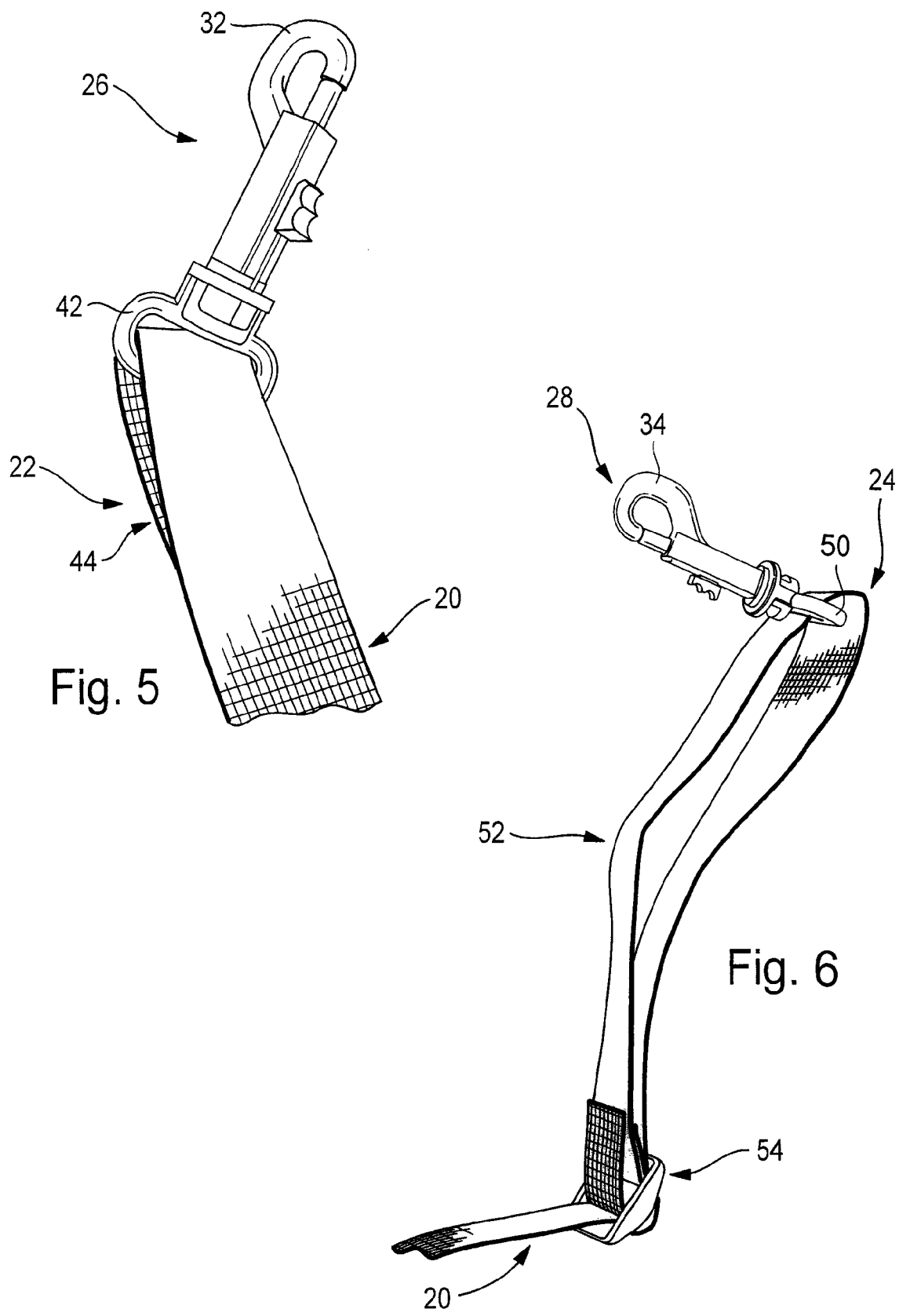

DEVICE FOR PROVIDING A VACUUM FOR VACUUM WOUND TREATMENT COMPRISING A HOLDING OR CARRYING DEVICE

This application claims Paris Convention priority of DE 10 2011 076 868.8 filed Jun. 1, 2011 as well as benefit of 61/457,846 filed Jun. 17, 2011 the complete disclosures of which are hereby incorporated by reference.

BACKGROUND OF THE INVENTION

The invention concerns a portable device for providing a vacuum for medical vacuum treatment of a wound on the body of a person or of an animal, comprising a suction pump, which generates a vacuum and is located in a housing part of the device, wherein a connection is provided for a suction line that leads to the body such that vacuum communication can be established between the suction pump and the suction line that leads to the body, and with a holding or carrying device with two connecting sections on the housing, which are disposed on the housing part for connection to two strap-side connecting sections of a holding or carrying strap.

The above-mentioned definition "portable device" means that the patient can carry the device along so that he/she is mobile and his/her wound can nevertheless be permanently treated, i.e. without interruption. The portable device may thereby be held on the body of the patient and be carried along by means of a holding or carrying device. A portable device of the above-mentioned type may naturally also be used for stationary operation, i.e. detached from the body of the patient. In this case, it may e.g. be mounted to a hospital bed or be deposited next to the hospital bed.

Vacuum wound treatment devices have been described many times, in particular, in US 2004/0073151 A1, WO 2009/047524 A2, WO 2007/030599 A2 or EP 1 905 465 A1, EP 777 504 B and in DE 10 2009 038 130 A1 and DE 10 2009 038 131 A1 of the assignee. The two latter publications already describe a portable device, wherein a strap-shaped section is mentioned as holding or carrying device for mobile operation, wherein this holding or carrying device can be removed for stationary operation of the device.

In devices of this type for vacuum treatment of wounds, a suction pump communicates via a suction line with the wound or the wound area, wherein a wound dressing with an air-tight cover is provided for air-tight sealing of the wound and the wound area, such that a vacuum can be generated in the wound region and fluids can be extracted by suction from the wound region.

The term vacuum in connection with the present invention defines an air pressure that is lower than the ambient air pressure (atmospheric air pressure), in particular, inside a wound dressing. The cover material of a wound dressing for air-tight sealing of a wound region must therefore be designed in such a fashion that it withstands the pressure difference that is established such that a vacuum can actually be applied to and maintained in the wound region. The wound dressing and the cover material are, however, typically flexible to a certain degree. In the field of vacuum therapy for the treatment of wounds, the vacuum is quantitatively defined as the pressure difference between ambient air pressure and the air pressure applied below the cover material. In the field of vacuum therapy, this pressure difference is typically at most 250 mmHg (mm mercury column) (1 mm Hg=1 Torr.=133.322 Pa). This vacuum range of up to maximally 250 mmHg has turned out to be suitable for wound healing. A preferred vacuum range is between 10 and 150 mmHg.

In a typical vacuum treatment, the vacuum that is applied to the wound by means of the device can either be kept substantially constant with time or can be varied with time, in particular, in cycles, which can be realized by a correspondingly designed and programmed control device for the vacuum-generating device, in particular, in dependence on further parameters.

An advantageously flexible suction line, e.g. in the form of a drainage hose, is provided for applying a vacuum and advantageously also for extracting body fluids, the drainage hose communicating at one end with the wound area or the wound region via a so-called port in the area of the wound cover material, and at the other end communicating with the vacuum-generating device, advantageously thereby interposing a container for receiving body fluids, in particular, wound exudates extracted from the wound by suction.

In addition to vacuum wound treatment, the present device may also be used for other applications for providing a vacuum for medical applications, in particular, extraction of any body fluids by suction, in the field of medical incontinence management, in the field of care of stoma patients or in the field of extraction of wound exudates, if necessary, thereby using rinsing liquids and also without application of a vacuum over considerable time periods.

Based on a portable device of this type for providing a vacuum for medical vacuum treatment of wounds, it is the underlying purpose of the present invention to further improve the handling quality of the device for stationary and mobile operation.

SUMMARY OF THE INVENTION

In accordance with the invention, this object is achieved with a device of this type in that the holding or carrying strap comprises a third strap-side connecting section, which is spaced apart from the opposing ends of the holding or carrying strap and from the first and second strap-side connecting sections disposed there and is arranged between these ends, for connection to one of the connecting sections on the housing and/or to one of the strap-side connecting sections disposed at the end.

The inventive device enables conventional use of the holding or carrying strap, i.e. by using two strap-side connecting sections which are arranged at the ends of the holding or carrying strap and can be connected to the connecting sections on the housing. This allows utilization of a maximum length of the holding or carrying strap, advantageously when a patient carries along the portable device.

The third strap-side connecting section permits reduction of the useful length of the holding or carrying strap in a simple fashion, i.e. by using one of the strap-side connecting sections arranged at the end for connection to one of the housing-side connecting sections and by using the third strap-side connecting section for connection to the other housing-side connecting section and/or for connection to the other strap-side connecting section disposed at the end.

The effective length of the holding or carrying strap can e.g. be altered by detaching a first or second strap-side connecting section disposed at the end from a housing-side section and instead connecting the third strap-side connecting section to the released housing-side connecting section.

Based on a state in which both strap-side connecting sections disposed at the end are connected to both housing-side connecting sections, the effective length of the holding or carrying strap can also be changed in that the third strap-side connecting section is additionally also connected to one of the two housing-side connecting sections, the third strap-side connecting section is connected to one of the two strap-side connecting sections disposed at the two ends, or the third strap-side connecting section is connected both to one of the two housing-side connecting sections and also to one of the two strap-side connecting sections that are arranged at the end.

Reducing the effective length of the holding or carrying strap is advantageous e.g. for carrying the portable device by hand. In this state, the housing of the portable device is closer to the carrying hand of a patient or medical staff due to the shortened holding or carrying strap. The shortened holding or carrying strap length may also be utilized, in particular, for mounting the portable device to an external carrier, e.g. a frame, in particular, a hospital bed, without thereby having to pay attention that the housing of the portable device does not come too close to the floor, which could result in undesired contact with legs or feet or also in soiling.

In one preferred embodiment of the invention, a first separation between the first strap-side connecting section and the third strap-side connecting section in a first strap section is shorter than a second separation between the third strap-side connecting section and the second strap-side connecting section in a second strap section. This is advantageous in that the maximum length of the holding or carrying strap can optionally be reduced to a first (smaller) separation or a second (larger) separation when the first strap-side connecting section and the second strap-side connecting section are used.

The separation between the first and the second strap-side connecting section is advantageously between approximately 50 and 160 cm.

The separation between the first and the third strap-side connecting section is advantageously between approximately 10 cm and 40 cm.

The separation between the second strap-side connecting section and the third strap-side connecting section is advantageously between approximately 40 cm and 120 cm.

The length of the first strap section is preferentially unchangeable, which further simplifies handling of the holding or carrying strap.

Moreover, an adjustment device is preferably provided for adjusting the length of the second strap section. This permits adjustment of the effective length of the holding or carrying strap, in particular, when the portable device shall be carried along in a conventional fashion on the body of a patient.

In one particularly preferred embodiment of the invention, a connecting device is provided for connecting the holding or carrying strap to an external carrier, in particular, a holding frame. The connecting device allows particularly reliable fixation of the portable device to the external carrier in such a fashion that the connecting device is connected both to the external carrier and to the holding or carrying strap. The holding or carrying strap itself is connected to the housing-side connecting sections of the housing part by means of at least two strap-side connecting sections.

Handling of the connecting device is particularly facilitated when the connecting device comprises a plug and/or snap connection.

In one preferred embodiment, the connecting device has a loop that can be closed and released at the peripheral side. This allows encircling arrangement of the loop around an external carrier, e.g. a bed frame, which is easy to produce.

The connecting device is advantageously arranged between the first strap-side connecting section and the third strap-side connecting section, in particular, when the separation between these connecting sections is smaller than the separation between the second strap-side connecting section and the third strap-side connecting section.

The connecting device can preferentially be operated independently of the connecting state of the strap-side connecting sections and the housing-side connecting sections. It is thereby possible to initially connect the holding or carrying strap to the housing part of the device and subsequently provide a connection to an external carrier by means of the connecting device. It is, however, also possible to initially connect the connecting device to the external carrier in order to subsequently connect two of the three strap-side connecting sections to the housing-side sections of the housing part.

In one embodiment of the invention, the holding or carrying strap comprises a supporting strap or carrier handle which is preferably arranged between the first strap-side connecting section and the third strap-side connecting section to further improve the wear comfort of the device. The supporting strap or carrier handle is designed e.g. in the form of a padded shackle.

The holding or carrying strap moreover advantageously comprises a shoulder support, which is advantageously arranged between the second strap-side connecting section and the third strap-side connecting section. This also further improves the wear comfort of the device.

Handling of the portable device is particularly facilitated when the strap-side connecting sections are designed in the form of automatically closing hooks (e.g. carabiners that are pretensioned by means of springs).

The holding or carrying strap can be fixed to the housing part with particular reliability when the housing-side connecting sections are designed in the form of lugs.

Preferred embodiments of the inventive device moreover comprise one or more of the following features:
- a container is provided for receiving body fluids, in particular, wound exudates that are extracted from a wound by suction;
- the container can be detachably fixed to the housing part of the device;
- the container can be evacuated by the suction pump in the mounted state;
- the vacuum communication between the suction pump and the suction line leading to the body can be established by interconnecting the container;
- a pressure sensor is provided, which is preferably disposed in a line section between the container and the suction pump for measuring the pressure;
- a programmable electronic control device is provided, which drives the suction pump at least thereby taking into consideration parameters that are and/or can be predetermined and pressure values measured by the pressure sensor;
- a rinsing device is provided for rinsing a wound to be evacuated.

Further features and advantages of the invention are the subject matter of the following description and the drawing that shows preferred embodiments.

BRIEF DESCRIPTION OF THE DRAWING

FIG. 5 shows an enlarged view of a section designated by V in FIG. 4;

FIG. 6 shows an enlarged view of a section designated by VI in FIG. 4;

DESCRIPTION OF THE PREFERRED EMBODIMENT

Figure 1:
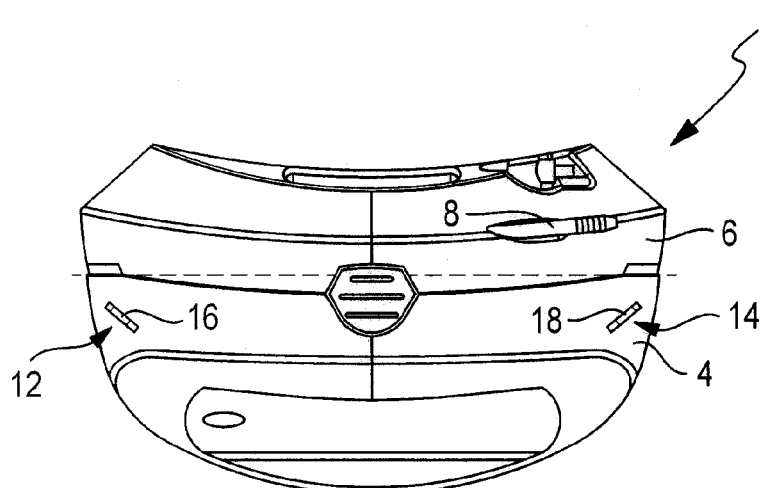
FIG. 1 shows a top view of an embodiment of a housing part of a portable device.
Figure 2:
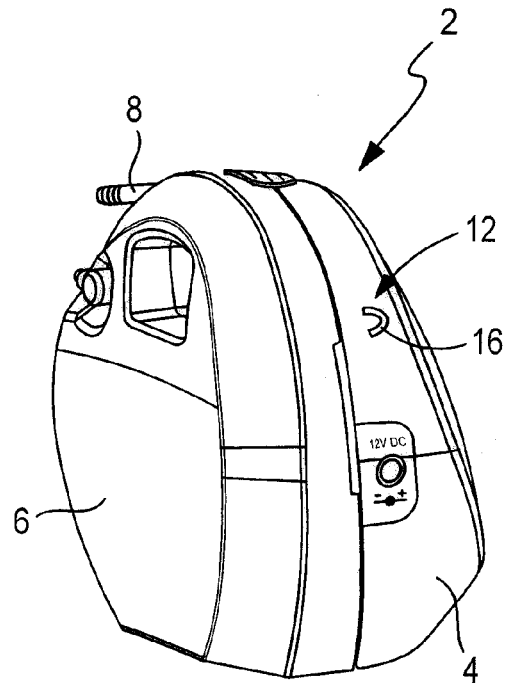
FIG. 2 shows a perspective view from the rear of the housing part in accordance with FIG. 1.
Figure 3:
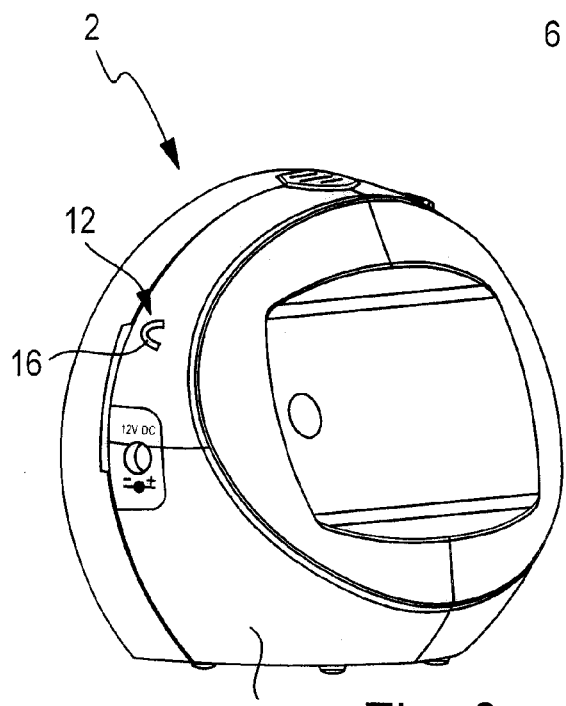
FIG. 3 shows a perspective view from the front of the housing part in accordance with FIG. 1.

An embodiment of a portable device is designated in total by reference numeral 2 in the drawing. The device 2 comprises a housing part 4 in which a suction pump (not illustrated) is arranged.

The housing part 4 is detachably connected to a container 6 for receiving body fluids. The container 6 can be connected via a connector 8 to a suction line that leads to a body, such that body fluid that is present in a wound area of a body can be extracted by the suction pump and be introduced into the container 6.

The device 2 comprises further components, e.g. a pressure sensor for measuring the pressure in a line section between the container and the suction pump and a programmable electronic control device which drives the suction pump, thereby at least taking into consideration the parameters that are and/or can be predetermined and the pressure values measured by the pressure sensor. With respect to the arrangement, the design and the function of these components and further components of the device 2, reference is made to the disclosure of DE 10 2009 038 130 A1, the entire disclosure of which is hereby incorporated by reference.

Figure 4:
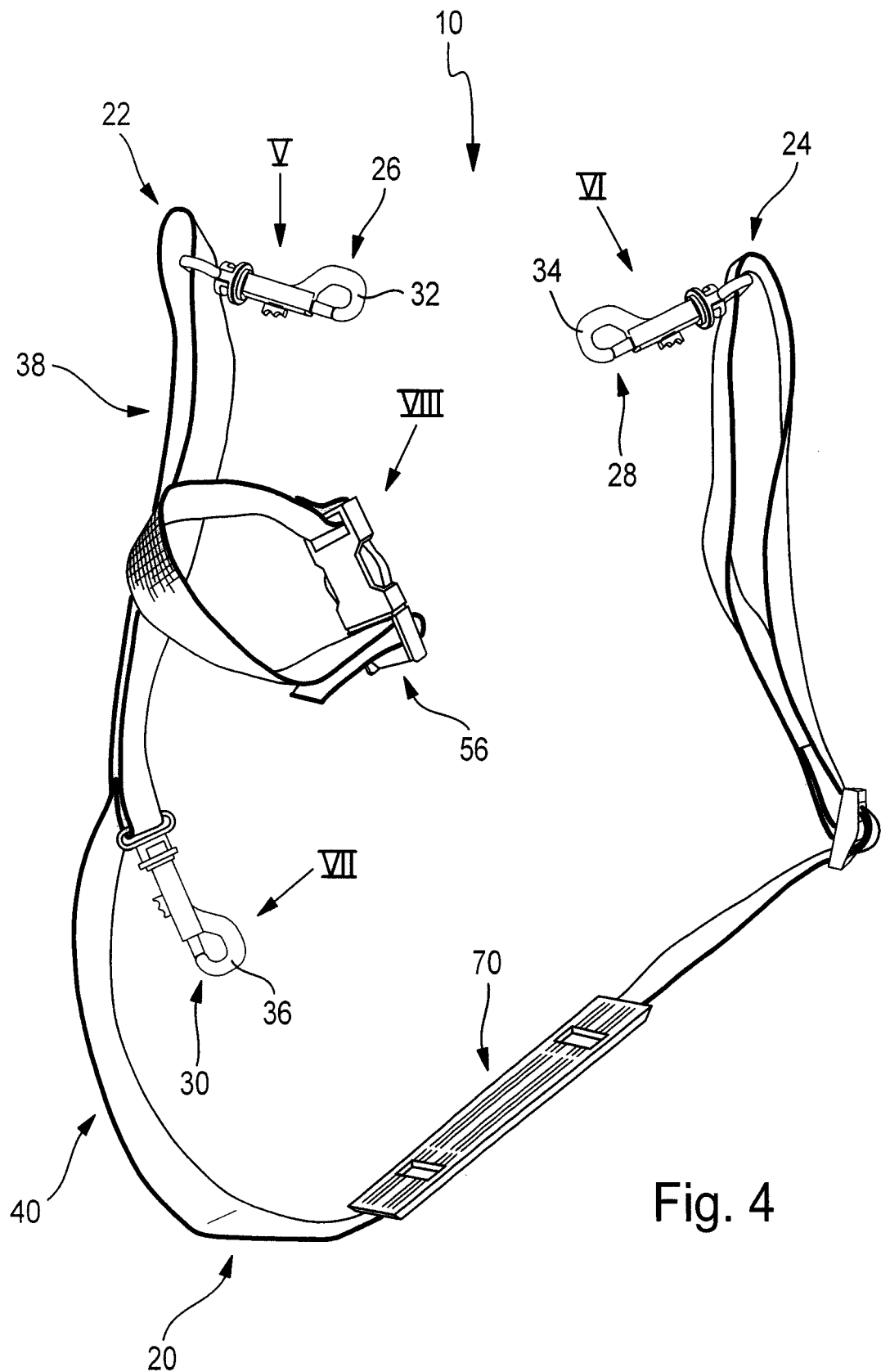
FIG. 4 shows a perspective view of an embodiment of a holding or carrying strap that can be detachably connected to the housing part.

The device 2 also comprises a holding or carrying device, which is illustrated in FIG. 4 and is designated therein in total by reference numeral 10.

The housing part 4 has two housing-side connecting sections 12, 14 for connection to the holding or carrying device 10. The connecting sections on the housing are designed in the form of lugs 16, 18.

The connecting sections 12, 14 on the housing are spaced apart from one another and are advantageously arranged in an area of the housing part 4 that is in the upper region during use.

The holding or carrying device 10 comprises a holding or carrying strap 20 having two opposing ends 22, 24. A first strap-side connecting section 26 is arranged at the first end 22 of the holding or carrying strap 20. A second strap-side connecting section 28 is arranged at the second end of the holding or carrying strap 20.

A further connecting section in the form of a third strap-side connecting section 30 is provided between the ends 22 and 24 as viewed along the extension of the holding or carrying strap 20.

The connecting sections 26, 28, 30 on the strap are designed, in particular, in the form of automatically closing hooks 32, 34, 36 (see FIGS. 4 to 7).

The holding or carrying strap 20 has a first strap section 38, which extends between the first connecting section 26 on the strap and the third connecting section 30 on the strap. The holding or carrying strap 20 moreover has a second strap section 40, which extends between the third connecting section 30 on the strap and the second connecting section 28 on the strap.

The length of the first strap section 38 defines a maximum separation between the first connecting section 26 on the strap and the third connecting section 30 on the strap. In a preferred embodiment, this length cannot be changed. Towards this end, the first connecting section 26 on the strap is mounted to a loop 44 of the holding or carrying strap 20 at an end by means of an annular holding section 42 (cf. FIG. 5).

Figure 7:
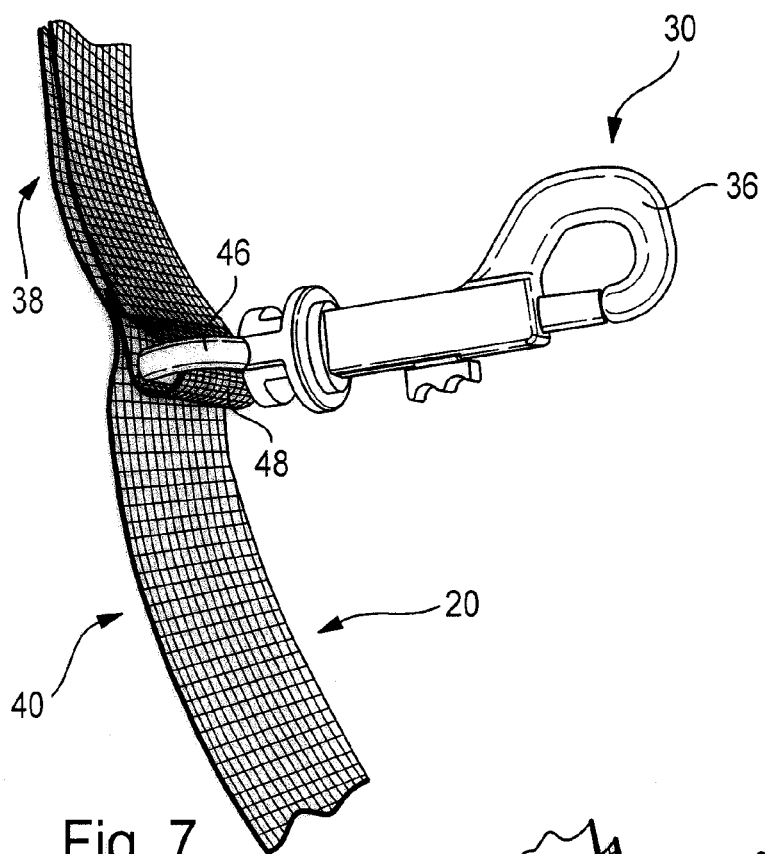
FIG. 7 shows an enlarged view of a section designated by VII in FIG. 4.

The third connecting section 30 on the strap also has an annular holding section 46, which is secured to a loop 48 of the holding or carrying strap 20 (cf. FIG. 7).

The geometry and, in particular, the loop length of the loops 44 and 48 cannot be changed. In contrast thereto, the second connecting section 28 on the strap (cf. FIG. 6) is secured to a loop 52 by means of an annular holding section 50, the length of the loop being adjustable by means of an adjustment device 54. The length of the second strap section 40 can also be adjusted by selecting the length of the loop 52, and therefore the overall length of the holding or carrying strap 20 can be adjusted.

Figure 8:
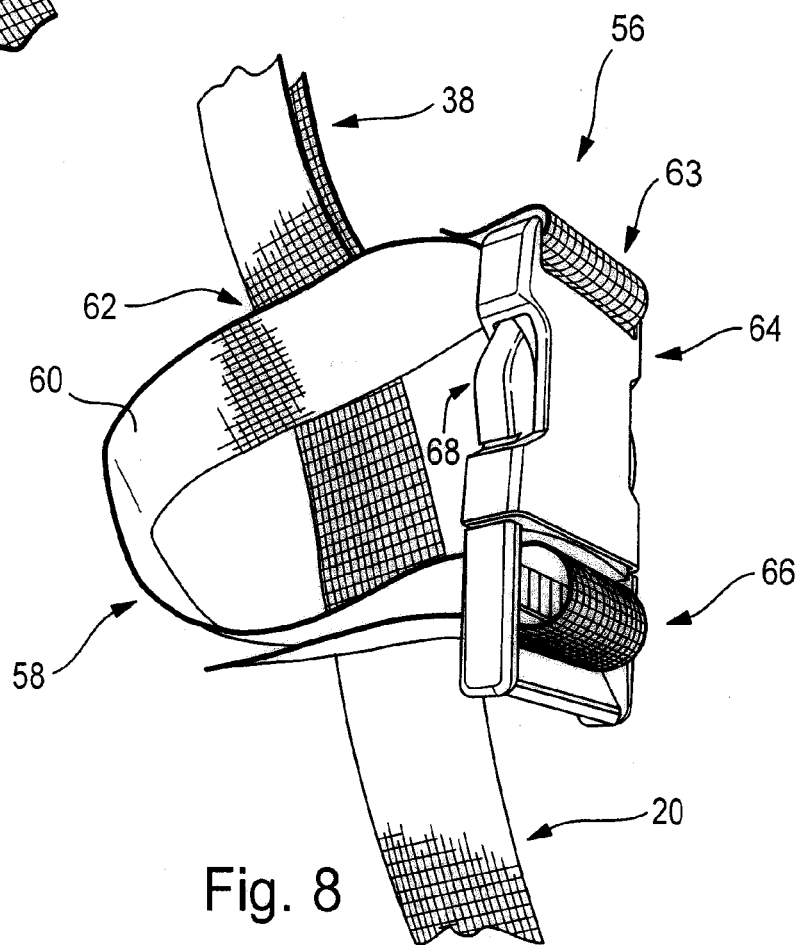
FIG. 8 shows an enlarged view of a section designated by VIII in FIG. 4.

A connecting device designated in total by reference numeral 56 is arranged in the first strap section 38 for connecting the holding or carrying strap 20 to an external carrier (not shown) (cf. FIGS. 4 and 8). The connecting device 56 comprises a loop 58 that can be closed and released on the peripheral side.

The loop 58 comprises a band 60 which is advantageously arranged transversely, in particular, perpendicularly with respect to the holding or carrying strap 20 and is, in particular, undetachably connected to the holding or carrying strap 20 in a connecting area 62. The band 60 has a first band end 62 for connection to a locking receptacle 64 and a second band end 66 for connecting to a locking plug 68. The locking plug 68 can be received in the locking receptacle 64 such that it locks and can be released again.

The effective length of the loop 58 can be adjusted in that the position of the second band end 66 relative to the locking plug 68 can be selected (the position of the first band end 64 relative to the locking receptacle 64 can be optionally or additionally selected).

During use of the device 2, the device can be carried along on the body of a patient by means of the holding or carrying device 10. The first and second connecting sections 26 and 28 may e.g. be connected to the connecting sections 12 and 14 on the housing. In this case, the effective length of the holding or carrying strap 20 is equal to the separation between the connecting sections 26 and 28 on the strap disposed at the end. For further improvement of the wear comfort, an e.g. rubberized shoulder support 70, which is arranged to be displaceable along the holding or carrying strap 20, can be positioned in such a fashion that it is supported on a shoulder of a patient.

In one further type of usage of the portable device 2, the connecting sections 26 and 30 on the strap are connected to the connecting sections 12 and 14 on the housing, or the third connecting section 30 on the strap is connected to the second connecting section 28 on the strap, while the latter is connected to one of the connecting sections 12 or 14 on the housing. In this way, the first strap section 38 can be used as a carrier handle for carrying the housing part 4. An additional, in particular, padded supporting strap or carrier handle (not shown) is optionally arranged in the first strap section 38.

The housing part 4 can also be connected to an external carrier by means of the connecting device 56. Towards this end, the loop 58 is arranged around a frame part of an external carrier. The effective length of the holding or carrying strap 20 is thereby preferably equal to the length of the first strap section 38 (cf. above paragraph). This yields a relatively short separation between the external carrier and the housing part 4.

We claim:

1. A portable device providing a vacuum for medical vacuum treatment of a wound on a body of a person or animal via a suction line leading to the body, the portable device being structured for attachment to an external carrier having a holding frame, such as a bed frame, the device comprising:

a suction pump, which generates a vacuum;

a housing part within which said suction pump is disposed, said housing part having a connection for the suction line to establish vacuum communication between said suction pump and the wound via the suction line, said housing part also having a first housing connecting section and a second housing connecting section; and a holding or carrying device, said holding or carrying device comprising a carrying strap having a first strap end and a second strap end, said carrying strap also having a first strap connecting section disposed proximate said first strap end and a second strap connecting section disposed proximate said second strap end, wherein said first strap connecting section is disposed, structured and dimensioned for connection to said first housing connecting section and said second strap connecting section is disposed, structured and dimensioned for connection to said second housing connecting section, said carrying strap also having a third strap connecting section, which is spaced apart from and disposed between said first and said second strap ends for connection to one of said first and said second housing connecting sections and/or to one of said first and said second strap connecting sections, said holding or carrying device also having a connecting device for connecting said carrying strap to the external carrier, wherein said connecting device has a loop which is structured to be closed and released on a peripheral side thereof, said connecting device being directly connected to said carrying strap at a portion of said carrying strap extending between and connecting together said first strap connecting section and said third strap connecting section.

2. The portable device of claim 1, wherein a first separation between said first strap connecting section and said third strap connecting section is shorter than a second separation between said third strap connecting section and said second strap connecting section.

3. The portable device of claim 2, wherein said first separation cannot be adjusted.

4. The portable device of claim 2, further comprising adjustment device for adjusting said second separation.

5. The portable device of claim 1, wherein said connecting device comprises a plug and/or snap connection.

6. The portable device of claim 1, wherein said connecting device is connected to said carrying strap in an undetachable fashion.

7. The portable device of claim 1, wherein said connecting device is operated independently of a state of connection of said first and said second strap connecting sections and independently of said first and said second housing connecting sections.

8. The portable device of claim 1, wherein said carrying strap has a supporting strap or carrier handle which is disposed between said first strap connecting section and said third strap connecting section.

9. The portable device of claim 8, wherein said carrying strap further comprises a shoulder support which is disposed between said second strap connecting section and said third strap connecting section.

10. The portable device of claim 1, wherein said first, second and third strap connecting sections are designed as automatically closing hooks.

11. The portable device of claim 1, wherein said first and second housing connecting sections are designed as lugs.

* * * * *